United States Patent [19]

Weikl et al.

[11] 4,311,136
[45] Jan. 19, 1982

[54] CATHETER CONNECTING HEAD WITH AT LEAST ONE DUCT IN A BASE MEMBER

[75] Inventors: Andreas Weikl; Max Hubmann, both of Erlangen, Fed. Rep. of Germany

[73] Assignee: Intermedicat GmbH, Emmenbrucke, Switzerland

[21] Appl. No.: 86,799

[22] Filed: Oct. 22, 1979

[30] Foreign Application Priority Data

Oct. 20, 1978 [DE] Fed. Rep. of Germany ....... 2845643

[51] Int. Cl.³ .............................................. A61M 5/00
[52] U.S. Cl. .......................... 128/214.4; 128/DIG. 16
[58] Field of Search ................ 128/349, 214 R, 214.4, 128/221, 348, 347, DIG. 16; 137/625.44

[56] References Cited

U.S. PATENT DOCUMENTS

| 3,434,691 | 3/1969 | Hamilton | 128/221 X |
| 3,739,778 | 6/1973 | Monestere, Jr. et al. | 128/214.4 |
| 3,851,647 | 12/1974 | Monestere, Jr. et al. | 128/214.4 |
| 3,915,168 | 10/1975 | Monestere, Jr. et al. | 128/214.4 |
| 4,126,133 | 11/1978 | Schwartz | 128/214.4 |

Primary Examiner—Stephen C. Pellegrino
Attorney, Agent, or Firm—Craig and Antonelli

[57] ABSTRACT

A catheter connecting head with at least one duct in a base member for the connection of an infusion system, such as a catheter or the like and for the introduction of a puncture cannula, is provided with a closure member mounted for movement between a first position opening the cannula introduction duct and a second position blocking said duct. The connecting head is provided with a device for retaining the closure member in the first position until the puncture cannula is withdrawn after which the closure element is automatically shifted into its second position. Once the closure member is in its second position blocking the cannula insertion duct, a locking arrangement retains the closure member in this position so that reintroduction of a puncture cannula into said insertion duct is not possible. In accordance with preferred embodiments, the closure member can be constructed as a lever member pivotally mounted to the base member or as a disc mounted upon the base member in a rotatable manner.

19 Claims, 17 Drawing Figures

CATHETER CONNECTING HEAD WITH AT LEAST ONE DUCT IN A BASE MEMBER

BACKGROUND AND SUMMARY OF THE INVENTION

The invention relates to a catheter connecting head with at least one duct in a base member for the connection of an infusion system.

In a conventional catheter of this type (DAS[German Published Application] No. 2,238,722), a hollow connecting piece consists of a catheter boss, a connecting boss for the infusion system or for a further catheter, and an elastic hose section arranged between both bosses. The wall of the hose section, which latter can be bent laterally, constitutes a zone of elastic, self-sealing material, for example, rubber, which can be penetrated by a hollow needle.

Apart from the fact that, when penetrating the rubber wall with the aid of a sharp tip of a metal cannula, there is no guarantee against scraping off rather small or extremely small parts of the rubber wall and preventing such parts from passing directly into the bloodstream, this conventional arrangement furthermore exhibits the danger that the rubber wall is once more penetrated by a metal cannula, thus damaging the catheter or the catheter insertion tube which had remained in the blood vessel from the first puncturing procedure.

Based on the above-described state of the art, the invention has an object of providing a catheter connecting head for a vein puncturing and self-retaining cannula kit, which connecting head, on the one hand, can be handled conveniently and safely as far as the physician is concerned and, on the other hand, reduces to a minimum or even entirely eliminates the danger of embolism or infection as far as the patient is concerned.

This object has been attained in a preferred embodiment according to this invention by the construction of the duct for the puncture cannula such that, upon withdrawal of the puncture cannula, the duct is automatically closed and locked by closure and locking elements such that reinsertion is not possible. Due to the fact that the puncture cannula duct is automatically sealed and closed when the puncture cannula is retracted and that this puncture cannula duct, as well as optionally additional ducts of the connecting head, are automatically sealed with respect to the surroundings with the aid of mechanical sealing elements, it is impossible to introduce additional puncture cannulas into the duct or ducts of the base member and thus already installed catheters cannot be accidentally damaged. Moreover, the sealing elements ensure that neither air bubbles nor any dirt particles can enter the bloodstream, whereby the danger of embolisms is substantially reduced.

These and further objects, features and advantages of the present invention will become more obvious from the following description when taken in connection with the accompanying drawings which shown, for purposes of illustration only, several embodiments in accordance with the present invention.

DETAILED DESCRIPTION OF THE PREFERRED EMBODIMENTS

Figure 1:
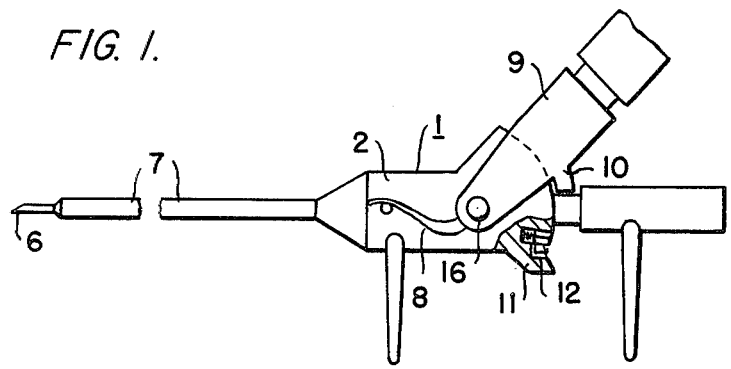
FIG. 1 shows, in a lateral view, a catheter connecting head with inserted puncture cannula.
Figure 2:
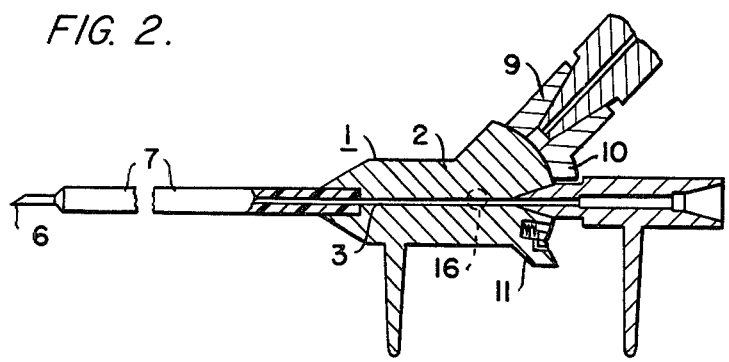
FIG. 2 shows a corresponding longitudinal section thereof.

The catheter connecting head 1 consists essentially of the base member 2 provided either merely with a single, straight duct 3 (FIGS. 1-5) or with additional ducts 4 and 5 (FIGS. 6-10b), the axes of which form a "Y" with respect to each other. In FIGS. 1 and 2, the puncture cannula 6 has been pushed through the catheter insertion tube 7, firmly joined to the base member 2, to such an extent that the puncture cannula 6 projects, in a manner known per se, for a small distance out of the catheter insertion tube 7.

Once the puncturing process is finished, the puncture cannula 6 is pulled out, thus freeing the path for the connecting and closure member 9 which is under the effect of a spring 8 which pivots the closure member until its nose 10 abuts against a stop 11 at the base member 2 (FIG. 3), simultaneously displacing a holding pin 12 for a locking pin 13 from its holding position. The locking pin 13 thus released is then caused to engage a recess 15 provided in the connecting and closure member 9 or in the nose 10 thereof under the influence of a spring 14. As a result, connecting and closure member 9 is prevented from changing its position.

To prevent the accidental insertion or operation of another puncture cannula 6 through the connecting and closure member 9 lying in its position aligned with duct 3 (FIGS. 3 and 4), this member 9 either has a corresponding length or is provided with a mounting cone which does not fit for puncture cannulas, so that the latter cannot be attached thereto.

The connecting and closure member 9 is pivotable about an axle 16 and is fashioned as a two-armed lever, wherein one lever arm can simultaneously be fashioned as the spring 8 while the other lever arm represents the connecting and closure member 9 proper, as shown in FIGS. 1 through 5.

Figure 2A:
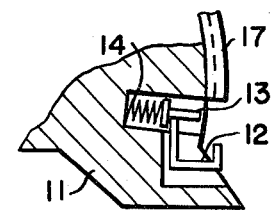
FIG. 2a shows, on an enlarged scale, the latched locking device in a plan view.
Figure 3:
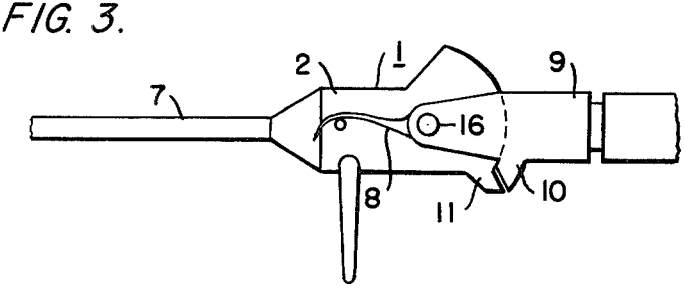
FIG. 3 shows, in a lateral view, a catheter connecting head with the puncture cannula having been pulled out and the closure element having been pivoted in position.
Figure 4:
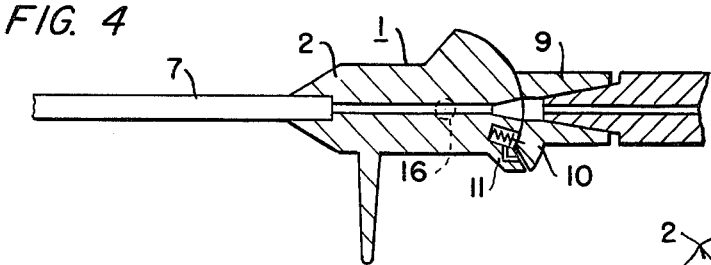
FIG. 4 shows a corresponding longitudinal section thereof.
Figure 4A:
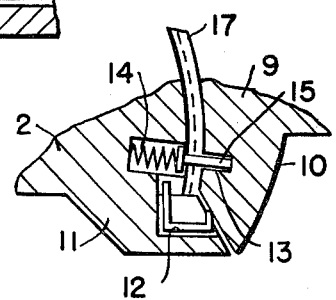
FIG. 4a shows, on an enlarged scale, the released locking device in a plan view.
Figure 5:
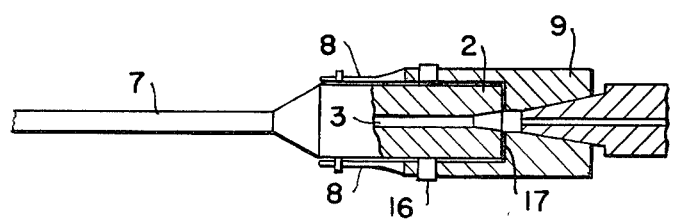
FIG. 5 shows a partial sectional view of the catheter connecting head in a top view.

The connecting and closure member 9 is sealed with respect to the base member 2 by way of gaskets of a conventional type, especially by way of ring seals 17 as indicated in FIGS. 2a, 4a, and 5. These gaskets prevent any outside air and any dirt particles from passing into the bloodstream.

Figure 6:
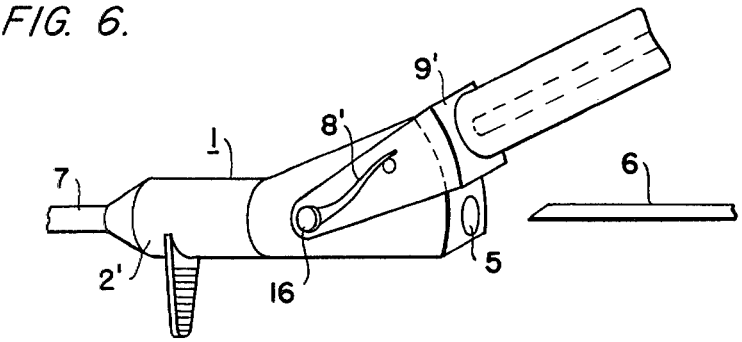
FIG. 6 shows in a perspective lateral view a catheter connecting head with a catheter attached to the closure member as a preparatory measure and with the puncture cannula still located on the outside.
Figure 7:
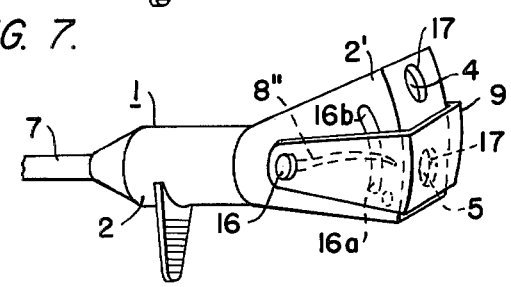
FIG. 7 shows, likewise, in a perspective lateral view, a catheter connecting head with the puncture cannula being pulled out and the closure element being pivoted in position, illustrating the locking feature and the sealing feature against the entrance of air.
Figure 7A:
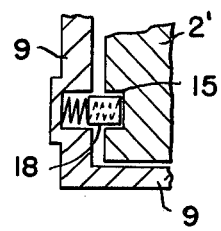
FIG. 7a shows the construction of the locking means on an enlarged scale.

As can be seen from FIGS. 6, 7, and 7a, pivotable connecting and closure member 9 can also be constructed as a one-armed lever. While, according to FIG. 6, the connecting and closure member 9' is operated by an externally disposed spring 8', this operation can also be effected, according to FIG. 7, by means of an interiorly disposed and thus covered spring 8". Also, in either case, the locking action can be executed by means of a spring bolt 18, which is shown in FIG. 7a on an enlarged scale and which locks into a recess 15 in the base member 2'. In this way, the mounting of a special stop at the base member 2 and the arrangement of a nose 10 at the connecting and closure member 9 can be omitted. The inwardly disposed spring element 8" according to FIG. 7 is arranged so that it is connected with one of its ends to the pivot axle 16 whereas its other end is guided at a stop 16a in a slotted hole 16b.

Figure 8:
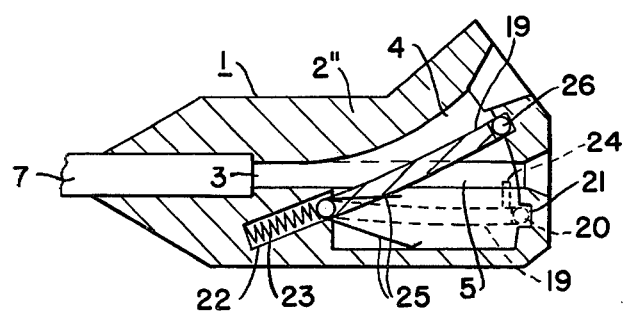
FIG. 8 shows in a lateral view a longitudinal section through a catheter connecting head with an inwardly positioned closure element, as well as its locking position.

FIG. 8 shows a catheter connecting head wherein the member sealing the duct 5 after the puncturing step is denoted by 19. Until the puncture cannula, not shown in the drawing, is introduced, the closure element 19 with the roller or ball 21 engaging the recess 20 is in the position shown in dashed lines wherein it is arrested by the effect of the compression spring 23 arranged in the bore 22. Only upon the introduction of the puncture cannula into the duct 5 does this cannula exert pressure on the dog 24 attached to the closure member 19 and thereby unlocks the closure element 19. As soon as the puncturing process is finished and the puncture cannula has been retracted from the duct 5, the closure element 19 jumps, under the action of the spring 25, into the position shown in solid lines and is locked in this position by the roller or ball 21 in the recess 26. Apart from the fact that now the duct 5 is permanently blocked for a reintroduction of a puncture cannula, the closure element 19 simultaneously serves as part of the wall for the duct 4, so that now a catheter, for example, can be readily introduced through this duct.

Figure 9:
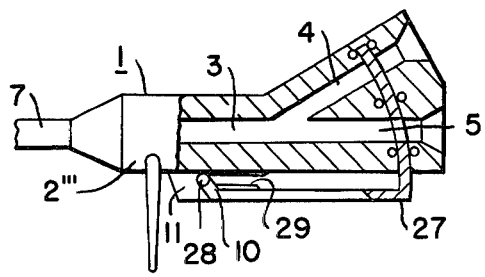
FIG. 9 shows a slide under the action of a spring in a position wherein only the insertion aperture for the puncture cannula is open.
Figure 9A:
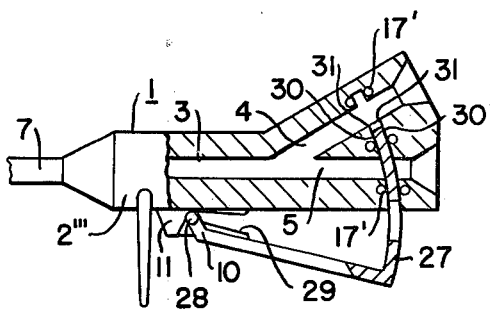
FIG. 9a shows the position of the slide wherein the introduction of a puncture cannula is no longer possible.
Figure 9B:
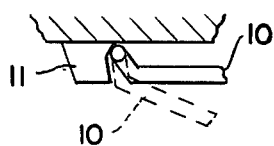
FIG. 9b shows on an enlarged scale a partial view of the two final positions of the slide linkage.

In FIGS. 9, 9a and 9b, a slide of a generally L-shaped configuration is provided as the closure element for ducts 4 and 5; this slide can be pivoted about the point 28 and is under the effect of the spring 29. By arranging the insertion opening in the slide 27 at the level of the duct 5 illustrated in FIG. 9a, it is also possible to effect the puncturing step in this slide position. The sealing of the slide 27 here again takes place, for example, by means of annular seals 17.

The slide 27 can be locked in the simplest way by one or more spreadable leaf springs 30 attached, for example, to the tip of the slide and contacting the undercut zones 31 upon retraction of the slide 27, as shown in FIG. 9a. Numeral 10 again denotes a nose contacting, in the locked position of the slide 27, the stop 11 as shown, in particular, in FIG. 9b.

Figure 10:
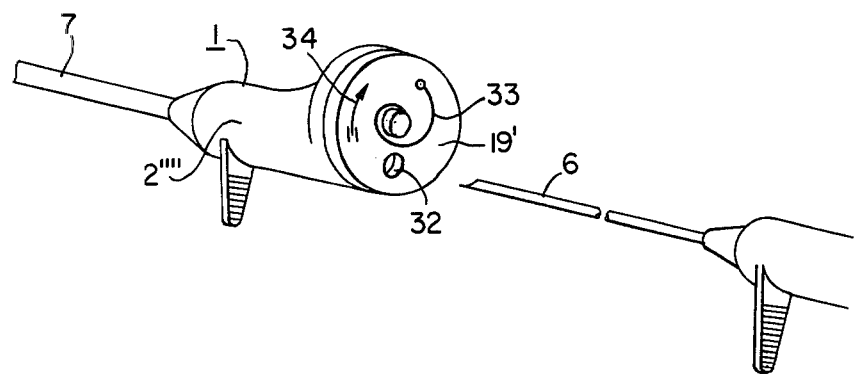
FIG. 10 shows a closure member as a rotatable disk with an eccentrically arranged bore in the introduction position for the puncture cannula.
Figure 10A:
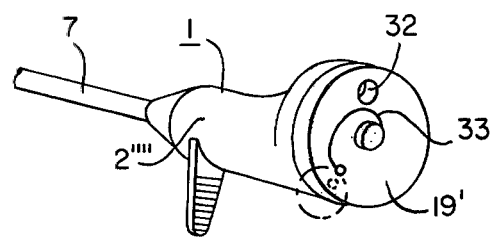
FIG. 10a shows the position of the disk-shaped closure member when the insertion aperture for the puncture cannula is blocked and the duct is opened for the introduction of a catheter or for the connection of an infusion system and FIG. 10b shows, on an enlarged scale, a plan view of the locking mechanism in the blocking position.
Figure 10B:
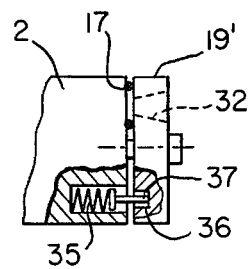

In FIGS. 10, 10a and 10b, the closure element 19 is fashioned as a rotatable disk 19' with an eccentrically arranged bore 32. In FIG. 10, the spiral spring 33 is tensioned, and the closure element 19' in the form of a disk can be locked in position in the same way as the closure element illustrated in FIG. 7a and denoted by 9. Upon introduction of the puncture cannula 6, the locking action is released and, after the puncture cannula 6 has been withdrawn, the disk is rotated under the effect of the spiral spring 33 in the direction of arrow 34. During this step, the pin 36, under the effect of the compression spring 35, automatically engages the recess 37 provided in the closure element 19 (FIG. 10b), so that the path for a puncture cannula 6 is also permanently blocked in this embodiment and all dangers inherent in the initially described, conventional devices are eliminated.

As compared with conventional catheter connecting heads, the invention is distinguished by a large number of advantages residing, in particular, in a simpler and substantially faster operability, due to the fact that the connecting and closure element is constantly in readiness. Moreover, assurance is obtained that, when changing over from the puncturing function to the catheter function, no air bubbles or even dirt particles can pass into the bloodstream. Also, operating errors, such as the unintended "puncturing" of already inserted catheters, can be safely excluded.

While we have shown and described various embodiments in accordance with the present invention, it is understood that the same is not limited thereto but is susceptible of numerous changes and modifications as known to those skilled in the art and we therefore do not wish to be limited to the details shown and described herein but intend to cover all such changes and modifications as are encompassed by the scope of the appended claims.

We claim:

1. Catheter connecting head with at least one duct and a base member for the connection of an infusion system, a catheter, or the like, and for introduction of a puncture cannula, comprising means for preventing re-introduction of a puncture cannula into a puncture cannula insertion duct, said means including a self-acting closure means for automatically closing the puncture cannula insertion duct upon withdrawal of the puncture cannula from the puncture cannula insertion duct, and self-acting locking means for securing the closure means in a closing and locking position.

2. Catheter connecting head according to claim 1, characterized in that the base member serves as a support for the closure and locking means.

3. Catheter connecting head according to claim 1, characterized in that the closure elements are simultaneously fashioned as connecting members for infusion devices.

4. Catheter connecting head according to one of claims 1, or 2 or 3, wherein the closure means comprises a closure element pivotally mounted upon said base member which is constructed as a two-armed lever, one lever arm of which acts as a spring for pivoting the closure element.

5. Catheter connecting head according to claim 4, wherein said locking means comprises a spring biased locking pin and retaining means therefor, said closure element during pivoting to an in-use position displacing said retaining means from a position holding said locking pin, whereby said locking pin is released into locking engagement with a corresponding recess in said closure element and thus retains the closure element in said closing and locking position.

6. Catheter connecting head according to claim 5, comprising a nose on the closure element, a stop on said base member, and spring means for displacing said closure element relative to said base member, after removal of the puncture cannula, until said nose engages said stop, fixing the closure element in a locking position.

7. Catheter connecting head according to claim 4, comprising a nose on the closure element, a stop on said base member, and spring means for displacing said closure element relative to said base member, after removal of the puncture cannula, until said nose engages said stop, fixing the closure element in a locking position.

8. Catheter connecting head according to claim 4, characterized in that, in a gap formed by the base member and the pivotable closure element, elastic sealing means are provided in the form of annular seals.

9. Catheter connecting head according to claim 1, wherein the closure means comprises a closure element pivotally mounted upon said base member which is constructed as a one-armed lever and a spring covered by the closure element, said spring being guided, on the one hand, on a pivot axle for the closure element and, on the other hand, upon a stop-member.

10. Catheter connecting head according to claim 9, wherein said locking means is mounted to the closure element and displaceable into engagement with a corresponding recess in the base member.

11. Catheter connecting head according to claim 1, wherein said closure means comprises a closure element, said closure element being displaceable from a first position, prior to the puncturing step, which is essentially in parallel to the duct for the puncture cannula to a second position blocking said duct; releasable locking means for retaining the closure element in said first position; a means for releasing said releasable locking means upon withdrawal of the puncture cannula, the closure element being brought into said second position blocking the duct for the puncture cannula upon release of said releasable locking means, said closure element simultaneously constituting a portion of a wall for a further duct when the closure element is in said second position.

12. Catheter connecting head according to claim 1, wherein said closure means comprises a pivotally displaceable closure element constructed as a generally L-shaped slide, a longer leg of which is articulated to the base member, a free end of a second, shorter leg being provided with at least one spreadable leaf spring forming said locking means which, during pivoting into a locking position, contacts undercut zones in the base member.

13. Catheter connecting head according to claim 1, wherein said closure means comprises a rotatably mounted closure element formed of a rotatable disk with a bore eccentrically positioned with respect to a disk axis of rotation for the introduction of the puncture cannula, releasable locking means for retaining said closure element in an open position, means for releasing said releasable locking means during introduction of the puncture cannula into the duct, and a spring for turning the closure element into said closing and locking position.

14. Catheter connecting head according to one of the claims 9-13 characterized in that, in a gap formed by the base member and the pivotable closure element, elastic sealing means are provided, in the form of annular seals.

15. A catheter connecting head comprising:
(a) a base member having a straight duct extending therethrough;
(b) a closure member mounted for movement between a first position in which the closure member is displaced from an inlet end of straight duct and a second position in which the closure member overlies said inlet end, said closure member being constructed such that a puncture cannula can be inserted into said inlet end to such an extent as to project from an opposite end of said straight duct when said closure member is in said first position, but not when the closure member is in the second position;
(c) resilient means connected to said closure member for displacing said closure member from said first position to said second position upon removal of a puncture cannula from said straight duct; and p1 (d) locking means carried by one of said closure and base members for locking said closure member in said second position.

16. A catheter connecting head according to claim 15, comprising an additional duct extending from an inlet end to said straight duct at an angle thereto, said closure member blocking the inlet end of the additional duct when it is in said first position, but not when it is in said second position.

17. A catheter connecting head according to claim 15 or 16, wherein said closure member is pivotally connected to said base member.

18. A catheter connecting head according to claim 15, wherein said closure member is provided with a through-passage for receiving a catheter.

19. A catheter connecting head according to claim 16, wherein said closure member is located within said base member and is engageable in recesses therein, said closure member being constructed and positioned so as to form a partition wall between said straight duct and said additional duct when in said second position.

* * * * *